(12) United States Patent
Potter (10) Patent No.: US 9,764,517 B2
(45) Date of Patent: Sep. 19, 2017

(54) OBJECT PRODUCTION USING AN ADDITIVE MANUFACTURING PROCESS AND QUALITY ASSESSMENT OF THE OBJECT

(71) Applicant: BAE SYSTEMS PLC, London (GB)

(72) Inventor: Mark Alfred Potter, Warton (GB)

(73) Assignee: BAE Systems plc, London (GB)

( * ) Notice: Subject to any disclaimer, the term of this patent is extended or adjusted under 35 U.S.C. 154(b) by 185 days.

(21) Appl. No.: 14/758,679

(22) PCT Filed: Jan. 6, 2014

(86) PCT No.: PCT/GB2014/050020
§ 371 (c)(1),
(2) Date: Jun. 30, 2015

(87) PCT Pub. No.: WO2014/106753
PCT Pub. Date: Jul. 10, 2014

(65) Prior Publication Data
US 2015/0336331 A1    Nov. 26, 2015

(30) Foreign Application Priority Data

Jan. 7, 2013  (EP) .................................... 13275002
Jan. 7, 2013  (GB) .................................... 1300171.4

(51) Int. Cl.
*B23K 26/00*  (2014.01)
*B29C 67/00*  (2017.01)
(Continued)

(52) U.S. Cl.
CPC ........ *B29C 67/0085* (2013.01); *B22F 3/1055* (2013.01); *B23P 6/00* (2013.01);
(Continued)

(58) Field of Classification Search
CPC ........... B22F 3/1055; B22F 2003/1057; B23K 26/00; B29C 67/0055; B29C 67/0059;
(Continued)

(56) References Cited

U.S. PATENT DOCUMENTS

2012/0201352 A1    8/2012  Dennerlein
2012/0224755 A1    9/2012  Wu

FOREIGN PATENT DOCUMENTS

CN    102522039 A    9/2012
DE    19817488 A     10/1999
(Continued)

OTHER PUBLICATIONS

GB Search Report for GB1300171.4 dated Jun. 28, 2013, 5 pages.
(Continued)

*Primary Examiner* — Leo B Tentoni
(74) *Attorney, Agent, or Firm* — Maine Cernota & Rardin (57) ABSTRACT

Methods and apparatus for producing and assessing at least part of an object (2), the methods comprise: performing, using Additive Manufacturing apparatus (8), an Additive Manufacturing process to produce a test specimen (30, 34, 38) and at least part of an object (2); performing, using micro-tomography apparatus (40), on the test specimen (30, 34, 38), a micro-tomography process to create a digital model (50) of the internal structure of the test specimen (30, 34, 38); determining whether or not the model (50) satisfies one or more criteria; and, if the model (50) satisfies the criteria, determining that the at least part of the object (2) produced by performing the Additive Manufacturing process is acceptable, or, if the model (50) does not satisfy the criteria, determining that the at least part of the object (2) produced by performing the Additive Manufacturing process is not acceptable.

11 Claims, 6 Drawing Sheets

(51) Int. Cl.
*B22F 3/105* (2006.01)
*G01N 23/00* (2006.01)
*G05B 19/418* (2006.01)
*G01N 23/04* (2006.01)
*G05B 19/401* (2006.01)
*B23P 6/00* (2006.01)
*B33Y 10/00* (2015.01)
*B33Y 30/00* (2015.01)
*B33Y 40/00* (2015.01)
*B29K 105/00* (2006.01)

(52) U.S. Cl.
CPC ...... *B29C 67/0077* (2013.01); *B29C 67/0088* (2013.01); *G01N 23/00* (2013.01); *G01N 23/046* (2013.01); *G05B 19/401* (2013.01); *G05B 19/41875* (2013.01); *B22F 2003/1056* (2013.01); *B29K 2105/251* (2013.01); *B33Y 10/00* (2014.12); *B33Y 30/00* (2014.12); *B33Y 40/00* (2014.12); *G01N 2223/419* (2013.01); *G01N 2223/6462* (2013.01); *G05B 2219/35352* (2013.01); *G05B 2219/45166* (2013.01); *G05B 2219/49021* (2013.01)

(58) Field of Classification Search
CPC ............ B29C 67/0066; B29C 67/0074; B29C 67/0077; B29C 67/0081; B29C 67/0088; G01N 23/046; G01N 2223/419; G01N 2223/6462; G05B 2219/35352; G05B 2219/45166; G05B 2219/49007; G05B 2219/49008; G05B 2219/49011; G05B 2219/49017; G05B 2219/49023; G05B 2219/49024
USPC ....... 264/40.1, 113, 308, 401, 497; 156/264, 156/272.8; 219/121.66, 121.85; 378/4, 378/21

See application file for complete search history.

(56) References Cited

FOREIGN PATENT DOCUMENTS

EP 1457853 A1 9/2004
WO 2008120183 A1 10/2008

OTHER PUBLICATIONS

European Search Report for EP13275002.7 dated Aug. 6, 2013, 9 pages.
Kruth J P et al: Computed tomography for dimensional metrology; CIRP ANNALS, vol. 60, No. 2, Jan. 1, 2011 (Jan. 1, 2011), pp. 821-842, XP028262022, ISSN: 0007-8506, DOI: 10.1016/J. CIRP. 2011.05.006.
Shawn Moylan et al: Proposal for a standardized test artifact for additive manufacturing machines and processes, Aug. 15, 2012 (Aug. 15, 2012), pp. 902-920, XP055073210, Retrieved from the internet: URL: http://www.nist.gov/customcf/get_pdf.cfm?pub_id=911953.

OBJECT PRODUCTION USING AN ADDITIVE MANUFACTURING PROCESS AND QUALITY ASSESSMENT OF THE OBJECT

RELATED APPLICATIONS

This application is a national phase application filed under 35 USC §371 of PCT Application No. PCT/GB2014/050020 with an International filing date of 6 Jan. 2014 which claims priority of GB Patent Application 1300171.4 filed 7 Jan. 2013 and EP Patent Application13275002.7 filed 7 Jan. 2013. Each of these applications is herein incorporated by reference in their entirety for all purposes.

FIELD OF THE INVENTION

The present invention relates to the production and assessment of objects or parts of objects.

BACKGROUND

Additive Manufacturing (AM) (also known as Additive Layer Manufacture (ALM), 3D printing, etc.) is a process that may be used to produce functional, complex objects, layer by layer, without moulds or dies. Typically, such processes include providing material (e.g. metal or plastic) in the form of a powder or a wire, and, using a powerful heat source such as a laser beam, electron beam or an electric, or plasma welding arc, melting an amount of that material and depositing the melted material (e.g. on a base plate of a work piece). Subsequent layers are then built up upon each preceding layer.

Example AM processes include, but are not limited to, Laser Blown Powder, Laser Powder Bed, and Wire and Arc technologies.

In a separate field, micro-tomography processes (which may also be referred to as X-ray micro-tomography, industrial computed tomography (CT) Scanning, and micro-CT scanning processes) are used to create three dimension virtual (or digital) models of internal and external structures of objects. Such process typically comprise using X-rays to create images of cross-sections of an object, which are then used to create a virtual model without destroying the original object.

Example micro-tomography processes include, but are not limited to, fan beam reconstruction processes and cone beam reconstruction processes.

SUMMARY OF THE INVENTION

In a first aspect, the present invention provides a method of producing and assessing at least part of an object. The method comprises: providing an initial object; performing, using common AM apparatus, an AM process to add additional material to the initial object, and produce a test specimen, the test specimen being produced from the same material as the additional material that is added to the initial object; performing, using micro-tomography apparatus, on the produced test specimen, a micro-tomography process to create a model (e.g. a 3-dimensional digital model), the model being a digital model of the internal structure of the test specimen; determining whether or not the model satisfies one or more criteria. If the model satisfies the one or more criteria, it may be inferred that the AM apparatus was operating as desired during all stages of the build process and, thus, that the additional material added to the initial object is acceptable. Alternatively, if the model does not satisfy the one or more criteria, it may be determined that the AM apparatus was not operating as desired at at least one stage of the build process and that consequently the additional material added to the initial object is not acceptable.

Advantageously, the micro-tomography apparatus and process facilitates the detection of very small voids or other defects in the test specimen. Such defects, which may occur in many AM processes, tend to be very difficult to detect using other techniques. For example, by moving the test specimen closer to a micro-tomography X-ray source and further from a screen upon which an X-ray image is projected, very small voids or other defects in the test specimen may be magnified.

Preferably, the test specimen is produced on a surface of the initial object at or proximate to the location, on the initial object, of the additional material that is added by the AM apparatus performing the AM process. This tends to provide that thermal characteristics of the test specimen are substantially the same as those of the additional material. For example, this tends to provide that heat dissipation within the test specimen is substantially the same as within the additional material. Also, this tends to provide that heat up and/or cool down rates of the test specimen are substantially the same those of the additional material. The test specimen having substantially the same thermal characteristics as the additional material tends to provide that the microstructure of the test specimen is representative (e.g. substantially the same as) that of the additional material. The microstructure of the test specimen may thus be analysed, using the micro-tomography apparatus and process, to approve or otherwise that of the additional material.

A portion of the test specimen may be produced, by the AM apparatus performing the AM process, before the AM apparatus has begun to add the additional material to the initial object. A portion of the test specimen may be produced, by the AM apparatus performing the AM process, after the AM apparatus has begun to add the additional material to the initial object and before the AM apparatus has finished adding the additional material to the initial object. A portion of the test specimen may be produced, by the AM apparatus performing the AM process, after the AM apparatus has finished adding the additional material to the initial object. Preferably, the test specimen comprises a first portion produced before the AM apparatus has begun to add the additional material to the initial object, a second portion produced after the AM apparatus has begun to add the additional material to the initial object and before the AM apparatus has finished adding the additional material to the initial object, and a third portion produced after the AM apparatus has finished adding the additional material to the initial object.

Having the test specimen include a portion produced before the AM apparatus has begun to add the additional material to the initial object tends to allow for (by analysing the microstructure of the test specimen) the verification or otherwise that the AM apparatus was operating as desired prior to the commencement of the AM process. Having the test specimen include a portion produced after the AM apparatus has begun to add the additional material to the initial object and before the AM apparatus has finished adding the additional material to the initial object tends to allow for (by analysing the microstructure of the test specimen) the verification or otherwise that the AM apparatus was operating as desired during the AM process. Having the test specimen include a portion produced after the AM apparatus has finished adding the additional material to the initial object tends to allow for (by analysing the microstructure of the test specimen) the verification or otherwise that the AM apparatus was operating as desired during the final stages of the AM process and afterwards. Thus, checking that the AM apparatus is operating as desired is facilitated. Conventionally, such verification tends to be very difficult due to the large number of variables involved in operating AM apparatus and performing AM processes.

The portions of the test specimen may be created as a stack of contiguous portions.

Each portion of the test specimen may have a different cross-sectional area to the one or more other portions with which that portion is contiguous.

The step of determining whether or not the model satisfies one or more criteria may comprise analysing the model to detect features in the model that correspond to defects (e.g. voids) with the test specimen, and determining whether or not the detected model features satisfy the one or more criteria.

Each of the one or more criteria may be a criterion selected from the group of criteria consisting of: a criterion that the total volume of the detected model features is below a first pre-determined threshold value; a criterion that the total surface area of the detected model features is below a second pre-determined threshold value; a criterion that the maximum volume of a detected model features is below a third pre-determined threshold value; a criterion that the maximum length of a detected model features is below a fourth pre-determined threshold value; a criterion that the total number of detected model features is below a fifth pre-determined threshold value; and a criterion that the detected model features are not arranged in a predetermined pattern.

The AM process may be a process selected from the group of AM processes consisting of: a blown powder AM process, a powder bed fusion AM process, a sheet lamination AM process, a vat photopolymerisation AM process, a laser blown powder AM process, a laser powder bed AM process, and an AM process that implemented wire and arc technology.

The method may further comprise, after the production of the test specimen, performing, using the AM apparatus, an AM process to produce a further test specimen; performing, using the micro-tomography apparatus, a micro-tomography process to create a further model, the further model being a digital model of the internal structure of the further test specimen; determining whether or not the further model satisfies the one or more criteria; wherein the at least part of the object produced by performing the AM process is only acceptable if the both the model and the further model satisfy the one or more criteria; and at least some of the at least part of the object is produced, by the AM apparatus performing the AM process, between the production of the test specimen and the production of the further test specimen.

In a further aspect, the present invention provides apparatus for producing and assessing at least part of an object, the apparatus comprising: Additive Manufacturing apparatus for performing an Additive Manufacturing process to, from the same material add additional material to an initial object and produce a test specimen; micro-tomography apparatus for performing, on the test specimen, a micro-tomography process to create a model, the model being a digital model of the internal structure of the test specimen; and one or more processors configured to: determine whether or not the model satisfies one or more criteria, and if the model satisfies the one or more criteria, determine that the additional material added to the initial object is acceptable, or, if the model does not satisfy the one or more criteria, determine that the additional material added to the initial object is not acceptable.

In a further aspect, the present invention provides a method of producing and assessing at least part of an object, the method comprising: performing, using common (i.e. the same) additive manufacturing (AM) apparatus, an AM process to produce, from common (i.e. the same) material (i.e. the same type of material) a test specimen (the test specimen being for use in a micro-tomography process) and at least part of an object; performing, using micro-tomography apparatus, on the produced test specimen, a micro-tomography process to create a model, the model being a digital model of at least some of the internal structure of the test specimen; determining whether or not the model satisfies one or more criteria; and, if the virtual model satisfies the one or more criteria, determining that the at least part of the object produced by performing the AM process is acceptable; or, if the virtual model does not satisfy the one or more criteria, determining that the at least part of the object produced by performing the AM process is not acceptable.

The method may further comprise, after the production of the test specimen, performing, using the AM apparatus, an AM process to produce a further test specimen; performing, using the micro-tomography apparatus, a micro-tomography process to create a further model, the further model being a digital model of the internal structure of the further test specimen; determining whether or not the further model satisfies the one or more criteria; wherein the at least part of the object produced by performing the AM process is only acceptable if the both the model and the further model satisfy the one or more criteria; and at least some of the at least part of the object is produced, by the AM apparatus performing the AM process, between the production of the test specimen and the production of the further test specimen.

A portion of the test specimen may be produced, by the AM apparatus performing the AM process, before the AM apparatus has begun to produce the at least part of the object.

A portion of the test specimen may be produced, by the AM apparatus performing the AM process, after the AM apparatus has begun to produce the at least part of the object and before the AM apparatus has finished producing the at least part of the object.

A portion of the test specimen may be produced, by the AM apparatus performing the AM process, after the AM apparatus has finished producing the at least part of the object.

The test specimen may comprise two or more portions selected from the group consisting of: a portion that is produced, by the AM apparatus performing the AM process, before the AM apparatus has begun to produce the at least part of the object; a portion that is produced, by the AM apparatus performing the AM process, after the AM apparatus has begun to produce the at least part of the object and before the AM apparatus has finished producing the at least part of the object; and a portion that is produced, by the AM apparatus performing the AM process, after the AM apparatus has finished producing the at least part of the object.

The portions of the test specimen may be created as a stack of contiguous portions.

Each portion of the test specimen may have a different cross-sectional area to the one or more other portions with which that portion is contiguous.

The step of determining whether or not the model satisfies one or more criteria may comprise analysing the model to detect features in the model that correspond to defects with the test specimen, and determining whether or not the detected model features satisfy the one or more criteria.

Each of the one or more criteria may be a criterion selected from the group of criteria consisting of: a criterion that the total volume of the detected model features is below a first pre-determined threshold value; a criterion that the total surface area of the detected model features is below a second pre-determined threshold value; a criterion that the maximum volume of a detected model features is below a third pre-determined threshold value; a criterion that the maximum length of a detected model features is below a fourth pre-determined threshold value; a criterion that the total number of detected model features is below a fifth pre-determined threshold value; and a criterion that the detected model features are not arranged in a predetermined pattern.

Producing the at least part of an object may comprise providing an initial object, and performing, using AM apparatus, the AM process to add additional material to the initial object, the additional material being the at least part of an object.

The test specimen may be produced on a surface of the initial object at a location that is proximate to the location, on the initial object, of the additional material that is added by the AM apparatus performing the AM process.

The AM process may be a process selected from the group of AM processes consisting of: a blown powder AM process, a powder bed fusion AM process, a sheet lamination AM process, a vat photopolymerisation AM process, a laser blown powder AM process, a laser powder bed AM process, and an AM process that implemented wire and arc technology.

In a further aspect, the present invention provides apparatus for producing and assessing at least part of an object, the apparatus comprising: AM apparatus for performing an AM process so as to produce a test specimen and produce at least part of an object; micro-tomography apparatus for performing, on the test specimen, a micro-tomography process to create a model, the model being a digital model of the internal structure of the test specimen; and one or more processors configured to determine whether or not the model satisfies one or more criteria, and, if the virtual model satisfies the one or more criteria, determine that the at least part of the object produced by performing the AM process is acceptable, or, if the virtual model does not satisfy the one or more criteria, determine that the at least part of the object produced by performing the AM process is not acceptable In a further aspect, the present invention provides a program or plurality of programs arranged such that when executed by a computer system or one or more processors it/they cause the computer system or the one or more processors to operate in accordance with the method of any of the above aspects.

In a further aspect, the present invention provides a machine readable storage medium storing a program or at least one of the plurality of programs according to the preceding aspect.

DETAILED DESCRIPTION

Figure 1:
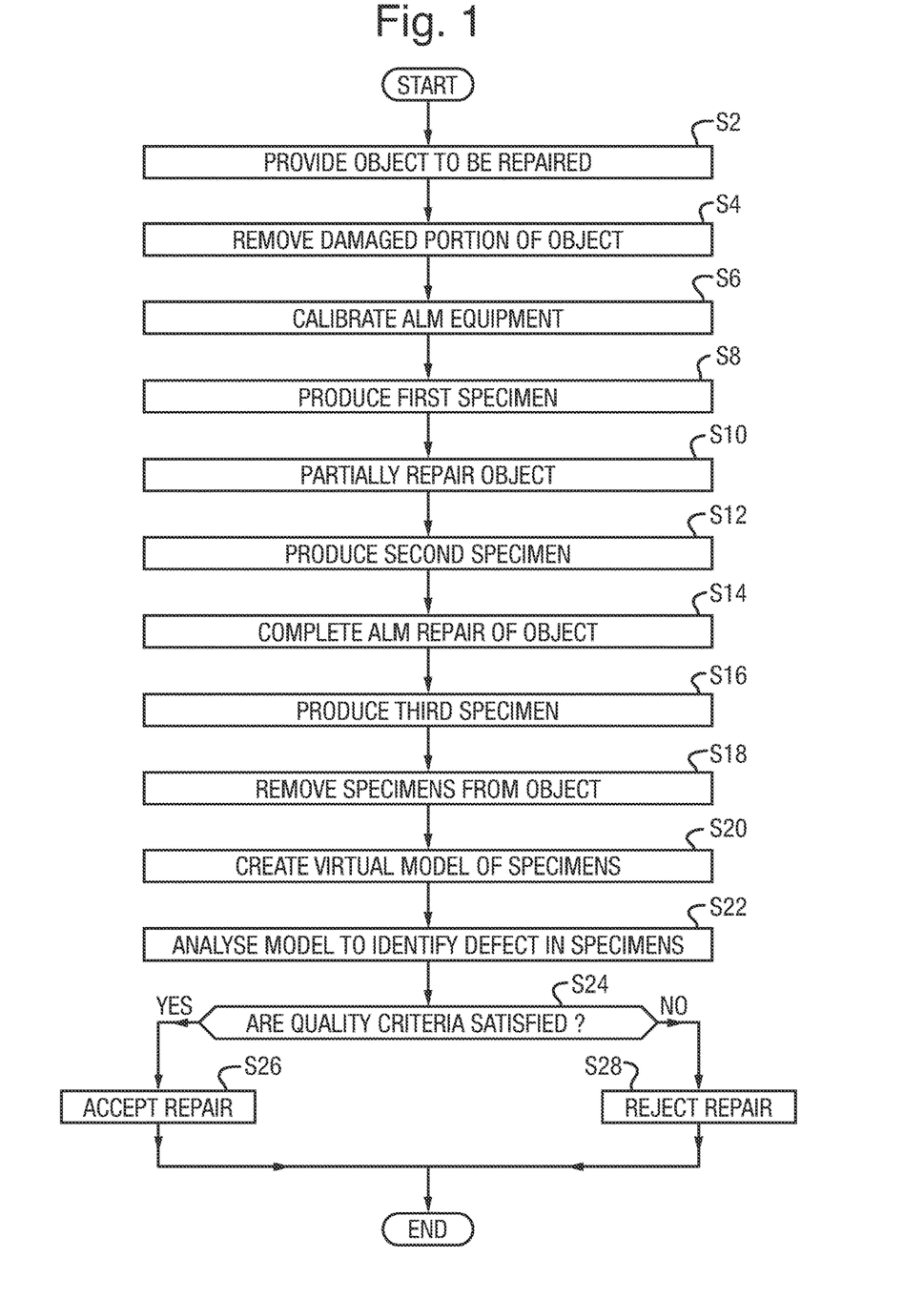
FIG. 1 is a process flow chart of an embodiment of a process of assessing quality or integrity of material produced using an additive manufacturing process.

FIG. 1 is a process flow chart of an embodiment of a process of assessing quality or integrity of material produced using an additive manufacturing (AM) process. In this embodiment, the AM process is performed to repair a damaged object.

At step s2, the damaged object that is to be repaired is provided.

Figure 2:
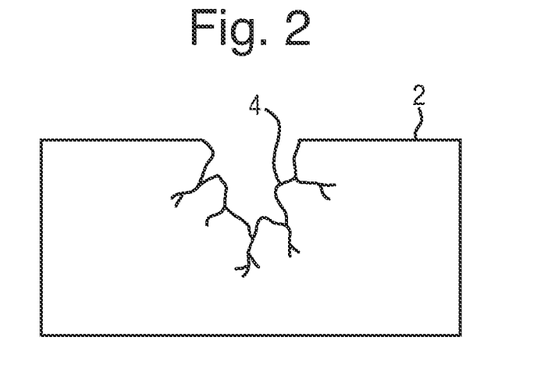
FIG. 2 is a schematic illustration (not to scale) showing a cross-section of the object.

FIG. 2 is a schematic illustration (not to scale) showing a cross-section of the object 2. A damaged portion of the object 2 is indicated in FIG. 2 by the reference numeral 4.

In this embodiment, the object 2 is made of metal. The object 2 may have been made using any appropriate process, for example, an additive manufacturing (AM) process, a near-net shape manufacturing process, etc. The object 2 may be any appropriate type of object, for example, a component part of a device or machine, such as an aircraft.

At step s4, the damaged portion 4 of the object 2 is removed. In this embodiment, this removal of the damaged portion 4 is performed by removing a portion of the object 2 such that no cracks (or feature that may act as crack initiators) are left in the object 2. In other words, the damaged portion 4 is "dressed out" from the object.

Figure 3:
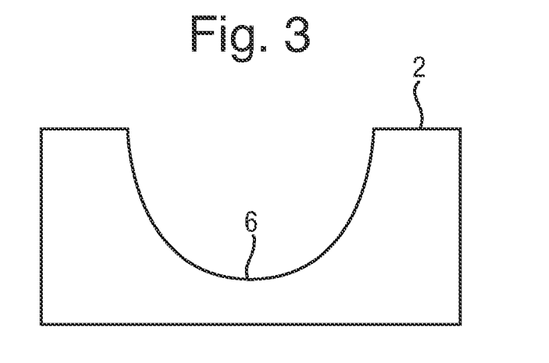
FIG. 3 is a schematic illustration (not to scale) showing the cross-section of the object after a damaged portion has been removed.

FIG. 3 is a schematic illustration (not to scale) showing the cross-section of the object 2 after the damaged portion 4 has been dressed out (e.g. by machining or cutting the damaged portion 4 away from the object 2). The void in the object 2 resulting from dressing out the damaged portion 4, i.e. from removal of the damaged portion 4, is hereinafter referred to as the "void" and is indicated in FIG. 3 by the reference numeral 6. It may be verified that all damage has been removed from the object, e.g. by performing a conventional Non-Destructive Testing (NDT) process on the object 2.

At step s6, the apparatus that will be used to perform the AM process to repair the object 2 is calibrated. The apparatus that will be used to perform the AM process to repair the object 2 is hereinafter referred to as the "AM apparatus" and is described in more detail later below with reference to FIG. 4.

This calibration process may, for example, include accurately measuring the damaged portion 4, and/or providing or creating a three dimensional model of the object 2 that is to be repaired. This data (i.e. the measurements of the damaged portion or the three dimensional model of the damaged object 2) may be used to generate a "tool path" (i.e. a path for the AM apparatus to follow) that will be used during the repair process. A "dry run" (i.e. a process in which the AM apparatus is moved along the tool path without applying heating or feedstock to the object 2) may be performed. This dry run process may be performed to establish that a geometrical clash condition does not exist, and/or also to ascertain as to whether or not the focal length of a laser of the AM apparatus is correct.

Optionally, values of further parameters of the AM process may also be determined. For example, a laser power density, a feedstock flow rate, X-Y positioning of the AM apparatus, and a melt pool temperature, etc. may be determined. Such parameter values may be determined by conducting an AM repair process on a test object (such as a piece of surplus material). The determined parameter values may be used to determine whether or not the AM apparatus is functioning within a specified tolerance range.

In this embodiment, the calibration of the AM apparatus remains the same throughout the process of FIG. 1, i.e. the AM apparatus is not re-calibrated during the process. However, in some embodiments, the AM apparatus is re-calibrated during the repair process, for example if the repair process is interrupted, e.g. by a power cut or mechanical failure.

At step s8, using an AM apparatus and by performing an AM process, a structure is built onto a surface of the object. This structure will hereinafter be referred to as the "first specimen". The first specimen is built proximate to the repair site. Thus, the heat dissipation characteristics of the test specimen are representative of those of the repair site.

Figure 4:
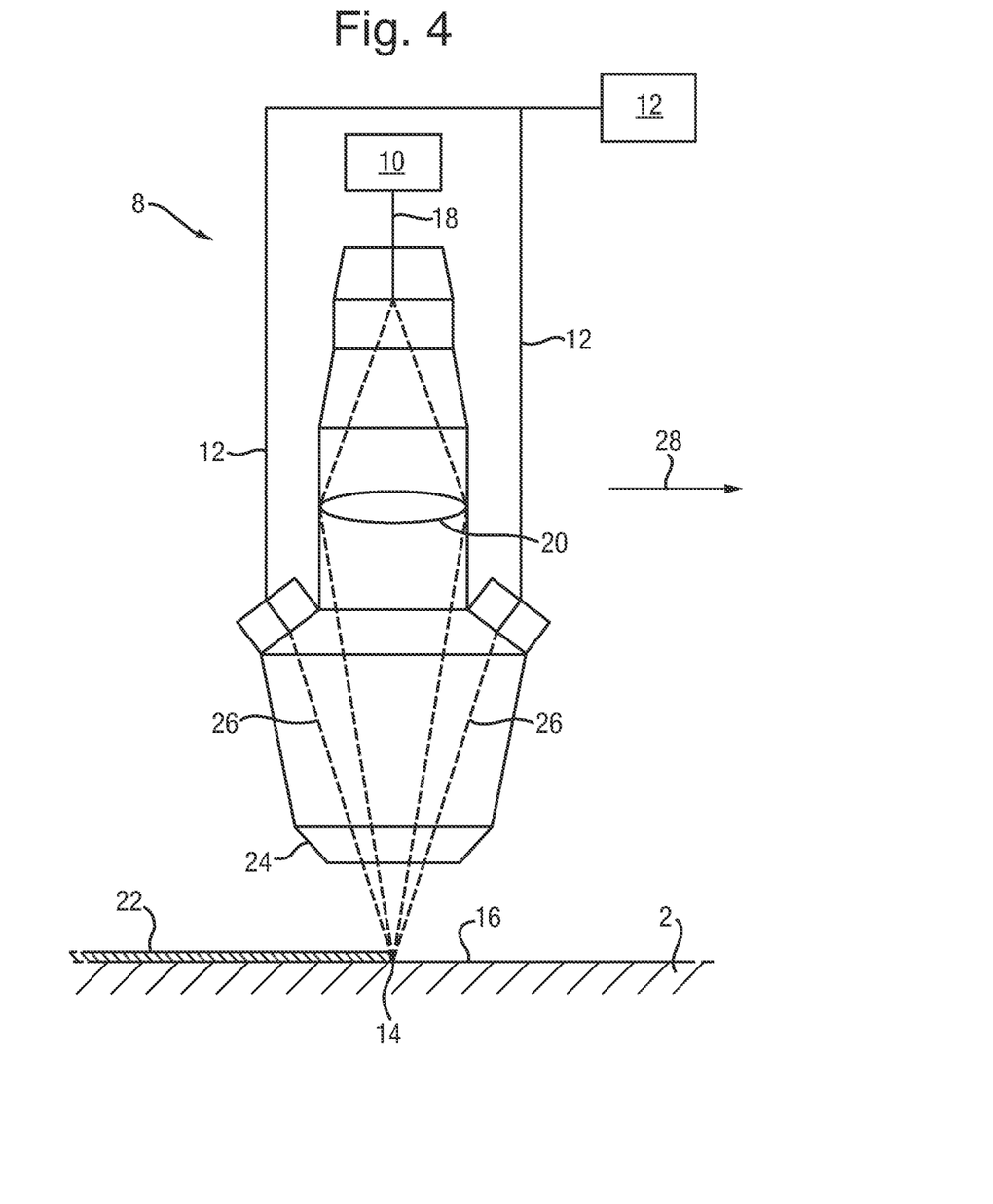
FIG. 4 is a schematic illustration (not to scale) showing the additive manufacturing apparatus.

What will now be described, with reference to FIG. 4, is the AM apparatus used in this embodiment, and the AM process performed in this embodiment, to create the first specimen. The first specimen is described in more detail later below with reference to FIG. 5, after the description of FIG. 4.

FIG. 4 is a schematic illustration (not to scale) showing the AM apparatus 8 being used to create a structure on the object 2 by performing an AM process on the object 2.

The AM apparatus comprises a heat source in the form of a high powered laser 10, a source of metallic material in the form of a powder delivery system 12. The AM apparatus further comprises cooling means in the form of a forced cooling nozzle (not shown in the Figure).

The laser 10 may be any appropriate type of laser, for example, an Nd:YAG laser that may operate at a wavelength of 1064 nm, and have a continuous wave power output of 500 W.

The laser 10 is focused upon a focal point 14 on an upper surface 16 of the object 2, whereby to melt the surface 16 to form a weld pool. The laser 10 is controlled by a computer (not shown in the Figures) to deliver a laser beam via an optical fibre 18 to conventional focussing optics 20 which focus the laser beam to the focal point 14 on the surface 16 of the object 2.

The powder delivery system 12 delivers powder to the vicinity of the laser focal point 14. Thus, the powder is fully melted as it is deposited on the work piece surface 16 to form a layer or bead 22. In this embodiment, the powder is a titanium powder. The powder grains may, for example, have a diameter between 36 μm and 106 μm. The powder delivery system 12 delivers powder through a deposition nozzle 24, along a plurality of delivery lines 26 which may be disposed symmetrically around the deposition nozzle 24. In other embodiments, a different type of material (e.g. a different type of metallic power e.g. stainless steel 316 powder) may be used.

In this embodiment, the AM apparatus 8 is moveable under the control of the computer in the X-Y plane that is parallel to the surface 16 of the object 2, and vertically in the Z direction orthogonal to the surface 16. Thus, the laser focal point 14 may be directed to any point in a working envelope in the X-Y plane and vertically so as to accommodate both work pieces of different height and also regions of different height within work pieces. In other words, in this embodiment, the AM apparatus is a 3-axis AM machine. In other embodiments, the Am apparatus 8 is a different type of AM machine, e.g. a 5-axis AM machine.

During operation, the AM apparatus 8 moves in a traverse direction, relative to the object 2, which is indicated by an arrow 28.

In this embodiment, the bead 22 is cooled to a crystallised state using the forced cooling gas nozzle e.g. using air or a cryogenic spray jet.

Many beads may be laid down beside one another and built on top of each other to form the repair and first specimen.

Figure 5:
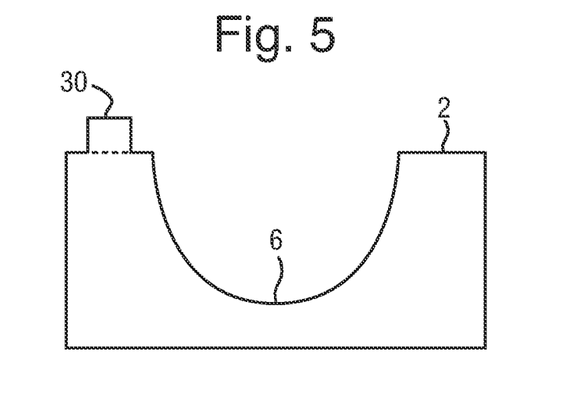
FIG. 5 is a schematic illustration (not to scale) showing the cross-section of the object after a first specimen has been produced.

FIG. 5 is a schematic illustration (not to scale) showing the cross-section of the object 2 after the first specimen 30 has been produced on a surface of the object 2.

In this embodiment, the first specimen 30 is built, on a surface of the object 2, remote from void 6 so that, as described in more detail later below, the void 6 may be filled (i.e. repaired) without the first specimen 30 obstructing the filling of the void 6, and so that the first specimen 30 may be removed, i.e. cut from, the object 2 without affecting the filled void 6. A layer of material between the first specimen 30 and the object 2 may also be built (using the AM process) that may be cut away so as to separate the first specimen 30 from the object 2.

Preferably, the first specimen is relatively small compared with the object 2. Also, preferably the first specimen 30 is a relatively simple shape to produce using the AM process. In this embodiment, the first specimen 30 is a cylinder having a diameter of 5 mm to 10 mm (e.g. 6 mm) and a length of 3 mm to 6 mm (e.g. 3.33 mm).

Thus, at step s8 a specimen, or test piece of material, is created before the AM apparatus 8 performs an AM process to repair the object 2.

At step s10, the object 2 is "partially repaired" by partially filling the void 6 using an AM process to deposit layers of material within the void.

In this embodiment, the void 6 is partially filled by, using the above described the AM apparatus 8, performing an AM process to build up layers of material within the void 6 until the void is partially filled with layers of material. The terminology "partially filled" is used herein to refer to a state in which the void has been filled to some degree, but has not been wholly filled.

Figure 6:
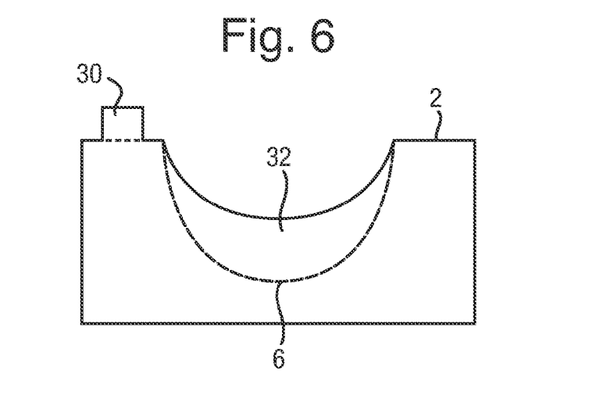
FIG. 6 is a schematic illustration (not to scale) showing the cross-section of the object after a void in the object has been partially filled.

FIG. 6 is a schematic illustration (not to scale) showing the cross-section of the object 2 after the void 6 has been partially filled using an AM process (performed by the AM apparatus). In FIG. 6, the original level of the void 6 is indicated by a dotted line. Additional material that has been added at step s10, using an AM process, is hereinafter referred to as "first additional material" and is indicated in FIG. 6 by the reference numeral 32.

At step s12, using the AM apparatus 8 and by performing an AM process, a structure is built onto a surface of the first specimen 30. This structure will hereinafter be referred to as the "second specimen".

Figure 7:
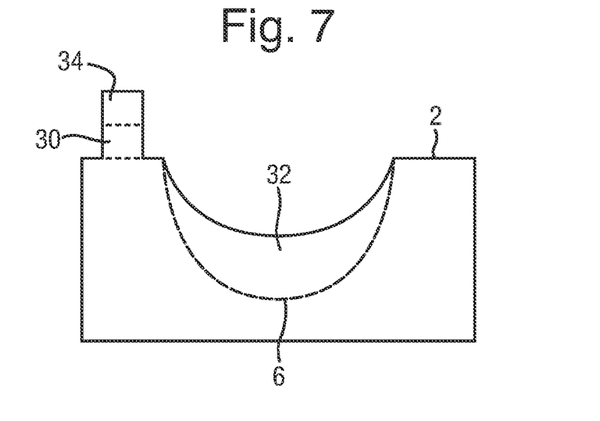
FIG. 7 is a schematic illustration (not to scale) showing the cross-section of the object after a second specimen has been produced.

FIG. 7 is a schematic illustration (not to scale) showing the cross-section of the object 2 after the second specimen 34 has been produced on a surface of the first specimen 30. The first specimen 30 and the second specimen 34 are separated in FIG. 7 by a dotted line.

In this embodiment, the second specimen 34 is built on top of the first specimen 30, i.e. such that the first specimen 30 and the second specimen 34 form a column, or stack, of material (e.g. of known thickness). The first and second specimens 30, 34 are contiguous with one another. The specimens 30, 34 are positioned remote from, but proximate to the void 6 (that has been partially filled with the first additional material 32) such that, as described in more detail later below, the void 6 may be further filled (i.e. completely filled) without the specimens 30, 34 obstructing the filling of the void 6, and so that the specimens 30, 34 may be removed, i.e. cut from, the object 2 without affecting the filled void 6.

Preferably, the second specimen 34 is relatively small compared with the object 2. Also, preferably the second specimen 34 is a relatively simple shape to produce using the AM process. In this embodiment, the second specimen 34 has the same length (i.e. 3 mm to 6 mm. e.g. 3.33 mm) as the first specimen 30. Also, in this embodiment, the cross-sectional shape of the second specimen 34 is different to that of the first specimen 30. In particular, the second specimen 34 has a square cross section, in contrast to the round cross section of the first specimen 30. In this embodiment, the width of the second specimen 34 is substantially the same as the diameter of the first specimen 30 (i.e. 5 mm to 10 mm, e.g. 6 mm).

Thus, at step s12 a specimen, or test piece of material, is created after the AM apparatus 8 has started repairing the object 2 (by depositing material, using the AM process, into the void 6), but before the AM apparatus 8 has completely repaired the object 2.

At step s14, the remainder of the void 6 is filled. In other words, the partially filled void 6 is filled such that the void 6 is completely filled. In this embodiment, this is performed by using an AM process to deposit layers of material within the void 6, onto the first additional material 32.

In this embodiment, the void 6 is filled by, using the above described the AM apparatus 8, performing an AM process to build up layers of material within the void 6, on top of the first additional material 32, until the void 6 is completely filled with layers of material. The terminology "completely filled" is used herein to refer to a state in which the void 6 has been wholly filled. In some embodiments, the void 6 is over-filled and the excess material machined, or cut, away at a later stage.

Figure 8:
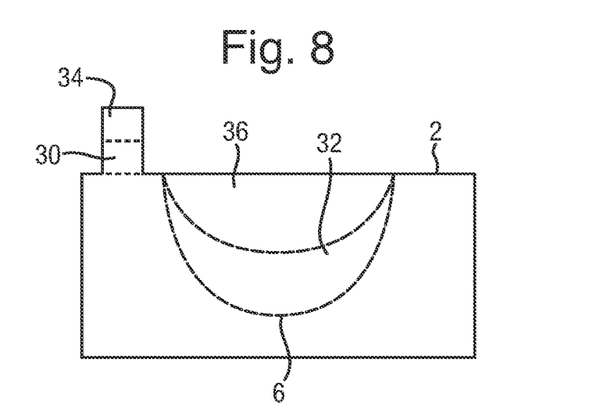
FIG. 8 is a schematic illustration (not to scale) showing the cross-section of the object after the void has been completely filled.

FIG. 8 is a schematic illustration (not to scale) showing the cross-section of the object 2 after the void 6 has been completely filled using an AM process (performed using the AM apparatus 8). In FIG. 8, the original level of the void 6 is indicated by a dotted line. The material that has been added at step s12 on top of the first additional material, using an AM process, is hereinafter referred to as "second additional material" and is indicated in FIG. 8 by the reference numeral 36.

At step s16, using the AM apparatus 8 and by performing an AM process, a structure is built onto a surface of the second specimen 34. This structure will hereinafter be referred to as the "third specimen".

Figure 9:
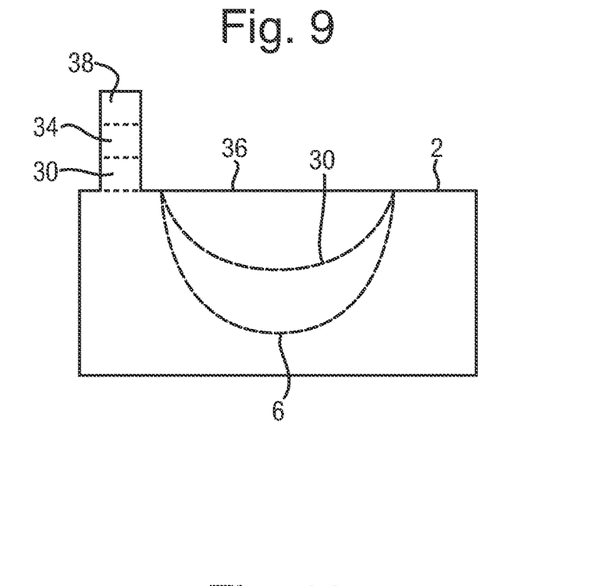
FIG. 9 is a schematic illustration (not to scale) showing the cross-section of the object after a third specimen has been produced.

FIG. 9 is a schematic illustration (not to scale) showing the cross-section of the object 2 after the third specimen 38 has been produced on a surface of the second specimen 34. The second specimen 34 and the third specimen 38 are separated in FIG. 9 by a dotted line.

In this embodiment, the third specimen 38 is built on top of the second specimen 34, i.e. such that the first specimen 30, the second specimen 34, and the third specimen 38 form a column, or stack, of material. The second and third specimens 34, 38 are contiguous with one another. The specimens 30, 34, 38 are positioned remote from the void 6 (that has been filled by the first additional material 32 and the second additional material 36) such that, as described in more detail later below, the specimens 30, 34 may be removed, i.e. cut from, the object 2 without affecting the filled void 6.

Preferably, the third specimen 38 is relatively small compared with the object 2. Also, preferably the third specimen 38 is a relatively simple shape to produce using the AM process. In this embodiment, the third specimen 38 is substantially the same size and shape as the first specimen 30, i.e. a cylinder having a length of 3 mm to 6 mm (e.g. 3.33 mm) and a diameter of 5 mm to 10 mm (e.g. 6 mm). Thus, in this embodiment, the cross-sectional shape of the third specimen 38 is different to that of the second specimen 34, but substantially the same as that of the first specimen 30.

Thus, at step s16 a specimen, or test piece of material, is created after the AM apparatus 8 has performed the AM process to repair the object 2.

At step s18, the specimens 30, 34, 38 are removed from the object 2. In this embodiment, the specimens are removed from the top surface of the object 2 by cutting the first specimen 30 (using any appropriate cutting device) at, or proximate to, the point where the first specimen 30 is attached to the object 2. In some embodiment, during the construction of the first specimen using the AM process (i.e. during step s8) a "sacrificial" layer of material may be formed between the first specimen 30 and the object 20. This sacrificial layer may be cut through at step s18, thereby separating the column of specimens 30, 24, 38 from the object 2.

At step s20, a three-dimensional virtual model of the column of specimens 30, 34, 38 (that was removed from the object 2 at step s18) is created. In this embodiment, the virtual model of the column of specimens 30, 34, 38 is created by performing a micro-tomography process, i.e. an Industrial Computed Tomography (CT) Scanning process.

In other words, at step s20 a digital three-dimensional representation of the external and internal structure of the column of specimens 30, 34, 38 is created.

Figure 10:
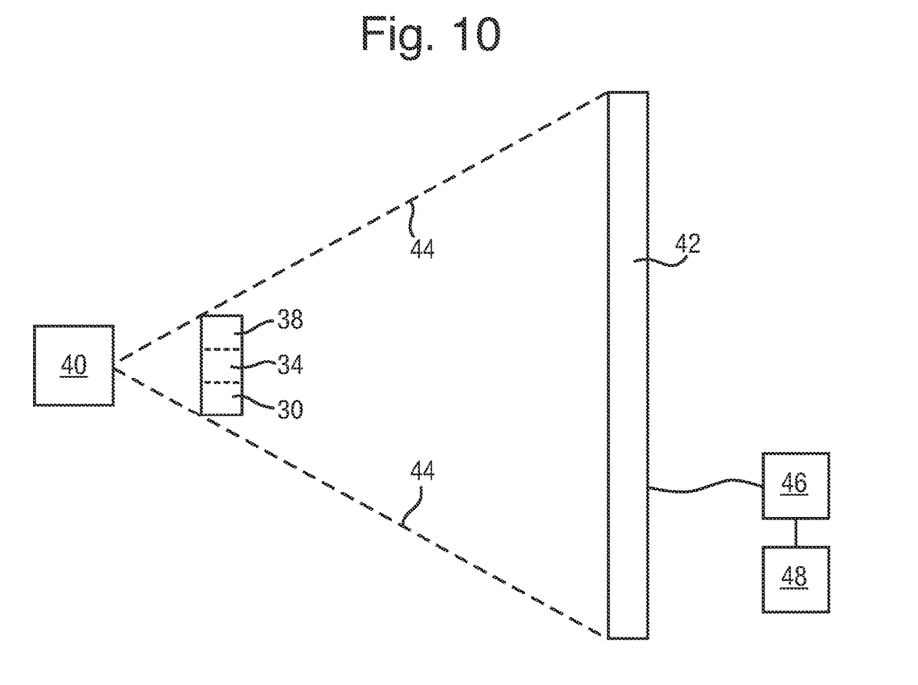
FIG. 10 is a schematic illustration (not to scale) showing micro-tomography apparatus performing a micro-tomography process on the specimens.

FIG. 10 is a schematic illustration (not to scale) showing a micro-tomography process being performed to create a three-dimensional virtual model of the external and internal structure of the column of specimens 30, 34, 38.

In this embodiment, an X-ray source 40 is positioned opposite to an X-ray detector 42. The object being scanned, i.e. the column of specimens 30, 34, 38, is located between the X-ray source 40 and the X-ray detector 42.

The X-ray source 40 emits X-rays 44 onto the column of specimens 30, 34, 38. The X-rays 44 that are incident on the column of specimens 30, 34, 38 are absorbed, to some extent, by the column of specimens 30, 34, 38. X-rays 44 that pass through the column of specimens 30, 34, 38 are incident on the detector 42. The detector 42 measures those X-rays 44 that are incident on it.

In this embodiment, X-ray images of the column of specimens 30, 34, 38 from different angles are obtained. This may be performed in any appropriate way. In one example method, the column of specimens 30, 34, 38 is rotated. In another example method, the X-ray source 40 and detector 42 are rotated around the column of specimens 30, 34, 38.

The measurements of the X-rays 44 taken by the detector 42 are sent, from the detector 42, to a processor 46. This processor 46 is configured to process the received X-ray images to create a three-dimensional virtual model of the external and internal structure of the column of specimens 30, 34, 38. Any appropriate processing method or software package may be used by the processor 46 to create the digital model. One example of an appropriate software package is the X-Tek™ software package 'Inspect-X'. The created three-dimensional virtual model can be viewed and manipulated using any appropriate tool, e.g. a software package such as the VGStudioMAX™ software package 'VGStudioMAX'.

The created three-dimensional representation of the column of specimens 30, 34, 38 is then sent, from the processor 46, to a display 48, where the model is displayed (e.g. to a human operator).

At step s22, the three-dimensional virtual model of the column of specimens 30, 34, 38 is analysed. This may be performed to identify defects (e.g. cavities, contamination etc.) within the column of specimens 30, 34, 38.

Figure 11:
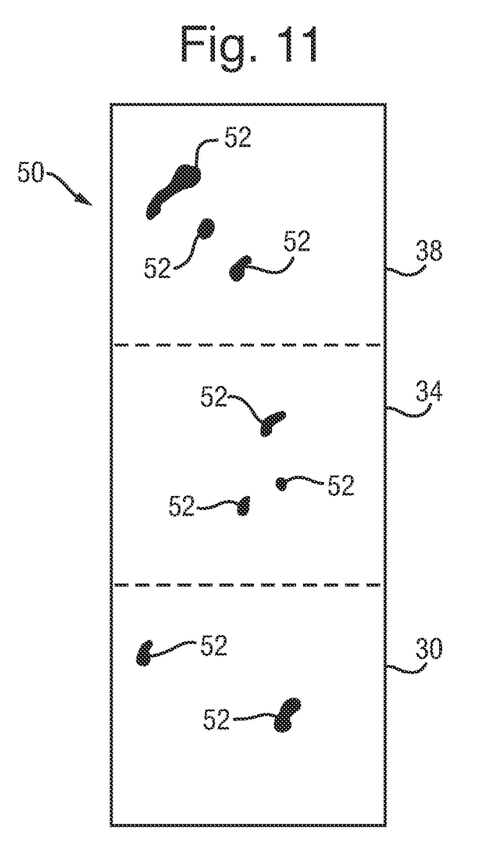
FIG. 11 is a schematic illustration (not to scale) of a cross section of a three-dimensional virtual model created by performing the micro-tomography process.

FIG. 11 is a schematic illustration (not to scale) of a cross section of the three-dimensional virtual model 50 created at step s20.

For convenience and ease of understanding, the portions of the model 50 that correspond to the first specimen 30, the second specimen 34, and the third specimen 38 have been indicated by the relevant reference numeral.

The column of specimens 30, 34, 38 may comprise one or more defects. These defects may, for example, be cavities or regions of contamination (e.g. caused by, during the AM process, the AM apparatus 8 melting a contaminant into the weld pool on the surface of the object 2). Cavities may, for example, contain a vacuum, or a substance (e.g. a gas) that is different to the metal material from which the column of specimens 30, 34, 38 is made. The regions of contamination may comprise a contaminant that is a different material to the metal material from which the rest of the column of specimens 30, 34, 38 is made. Thus, defects tend to have a different density than the material that forms the bulk of the column of specimens 30, 34, 38. Thus, the defects tend to absorb the X-rays 44 used to image the column of specimens 30, 34, 38 during the micro-tomography process differently, when compared to the material that forms the bulk of the column of specimens 30, 34, 38. Thus, defects in the column of specimens 30, 34, 38 may be detected by the micro-tomography process, and those defects tend to be visible in the created three-dimensional virtual model of the column of specimens 30, 34, 38. In the model 50 shown in FIG. 11, digital representations of the defects in the column of specimens 30, 34, 38 (hereinafter referred to as "the defects") are indicated by filled in shapes and the reference numeral 52.

The identification of the defects 52 in the model 50 may be performed using any appropriate process. For example, a human operator may, using the model 50 displayed to them on the display 48, identify the defects 52 within the model 50 that, e.g. correspond to defects in the column of specimens 30, 34, 38. Preferably, analysis of the model 50 to identify the defects 52 is performed automatically, e.g. by a computer (e.g. the processor 46). Analysis of the model 50 may comprise implementing any appropriate software or computer program, for example, the abovementioned Inspect-X™ software and/or VGStudioMAX software.

At step s24, using the model 50 and the analysis thereof, it is determined whether or not the specimens 30, 34, 38 satisfy one or more pre-determined quality criteria.

Any appropriate quality criteria may be used. An example quality criterion is the criterion that the total volume of the defects 52 in the model 50 (i.e. the total volume of defects in all of the specimens 30, 34, 38) is below a first pre-determined threshold value. A further example quality criterion is the criterion that the total volume of the defects 52 in the each specimen 30, 34, 38 is below a second pre-determined threshold value. A further example quality criterion is the criterion that the total surface area of the defects 52 in the model 50 (i.e. the total surface area of defects in all of the specimens 30, 34, 38) is below a third pre-determined threshold value. A further example quality criterion is the criterion that the total surface area of the defects 52 in the each specimen 30, 34, 38 is below a fourth pre-determined threshold value. A further example quality criterion is the criterion that the maximum volume of a defect 52 in the model 50 is below a fifth pre-determined threshold value. A further example quality criterion is the criterion that the maximum length of a defect 52 in the model 50 is below a sixth pre-determined threshold value. A further example quality criterion is the criterion that the number of defects 52 in the model 50 is below a seventh pre-determined threshold value. A further example quality criterion is the criterion that the number of defects 52 in each of the specimens 30, 34, 38 is below an eighth pre-determined threshold value. A further example quality criterion is the criterion that the defects 52 are not arranged in a predetermined pattern (e.g. in a line).

The different cross-sections of the specimens 30, 34, 38 advantageously tend to facilitate the distinguishing between specimens 30, 34, 38 in the digital model. Thus, this tends to facilitate determining which defects 52 occur in which of the specimens 30, 34, 38. This may, for example, be required when whether or not determining some of the quality criteria have been satisfied.

The determination as to whether or not the one or more pre-determined quality criteria are satisfied may be performed using any appropriate process. For example, a human operator may, using the model 50 displayed to them on the display 48, determine whether or not the quality criteria are satisfied. Preferably, the determination as to whether or not the one or more quality criteria are satisfied is performed automatically, e.g. by a computer (e.g. the processor 46).

If, at step s24, it is determined that the one or more pre-determined quality criteria are satisfied, the process of FIG. 1 proceeds to step s26.

However, if at step s24 it is determined that the one or more of the pre-determined quality criteria are not satisfied, the process of FIG. 1 proceeds to step s28, which will be described in more detail later below after the description of step s26.

At step s26, it has been determined that the one or more pre-determined quality criteria are satisfied, and, from this, it is inferred that, when creating the specimens 30, 34, 38, the AM apparatus 8 was operating acceptably, i.e. that material formed by the AM process during this time is acceptable.

From this, because the first specimen 30, the second specimen 34, and third specimen 38 were created, respectively, before, during, and after the deposition of material within the void 6, it is inferred that before, during, and after the deposition of material within the void 6, the AM apparatus 8 was operating acceptably, i.e. that material formed by the AM process during this time is acceptable.

Thus, it is inferred that the first additional material 32 and the second additional material 36 is acceptable.

Consequently, at step s26, the repair of the object 2 is accepted. The satisfactorily repaired object 2 may then be processed further, e.g. to machine away any excess or unnecessary material deposited during the repair process, or to smooth or polish the object 2. The object 2 may then be put into use.

After step s26, the process of FIG. 1 ends.

Returning now to the case where, at step s24, it is determined that the one or more of the pre-determined quality criteria are not satisfied, at step s28, it is inferred that, when creating the specimens 30, 34, 38, the AM apparatus 8 was operating not acceptably, i.e. that some or all material formed by the AM process during this time is not acceptable or substandard.

From this, because the first specimen 30, the second specimen 34, and third specimen 38 were created, respectively, before, during, and after the deposition of material within the void 6, it is inferred that, at some stage during the deposition of material within the void 6, the AM apparatus 8 was not operating acceptably and that some or all material formed by the AM process during this time is not acceptable.

Thus, it is inferred that some or all of either or both of the first additional material 32 and the second additional material 36 is not acceptable.

Consequently, at step s28, the repair of the object 2 is rejected.

The unsatisfactorily repaired object 2 may then be processed further. In this embodiment, after step s28, the process of FIG. 1 returns to step s4 where the first additional material 32 and the second additional material 36 added during the iteration are removed. In other words, after step s28, the material added to the void 6 is removed and the process of filling that void 6 (i.e. repairing the object 2) is restarted.

Thus, the process of FIG. 1 may be iterated until the object 2 has been repaired satisfactorily (i.e. until the quality criteria are satisfied).

Thus, an embodiment of a process of repairing a damaged object using additive manufacturing (AM) is provided.

The above described methods and apparatus advantageously implement AM processes to repair damaged objects. The above described methods and apparatus are advantageously equally applicable to instances in which AM process are implemented to create new objects, or add new features to existing objects. The portion of object created using AM processes advantageously tends to have similar or improved mechanical properties (such as good fatigue performance) compared to the base material on which the deposition is performed, i.e. the portions of that object not created during the AM repair processes.

The creation of the test specimens before, during, and after the repair of the object has been effected advantageously tends to provide that the quality of those test specimens is representative of the quality of the material deposited to repair the object. Thus, the quality of the repair may advantageously be assessed based on the quality of the test specimens.

Also, the use of the test specimens to assess the quality of the repair of the object advantageously tends to reduce or eliminate a need for the object itself having to be tested. Testing of the object tend to be difficult or costly, particularly for large objects. Also, the use of conventional quality assessment (e.g. using conventional non-destructive, or destructive, testing) may be reduced or eliminated.

The test specimens are created at or near the location of the object that is to be repaired using the AM process. This advantageously tends to reduce the distance through which the AM apparatus has to move when changing between creating a test specimen and depositing material so as to repair the object. Also, this advantageously tends to provide that the test specimens have similar heat dissipation characteristics to (i.e. is thermally representative of) the material that is deposited in the void (i.e. the repair material).

The test specimens are created one on top of another (i.e. in a stack or column). This advantageously tends to provide that the specimens may be removed from the object as a single piece. This also advantageously tends to provide that the micro-tomography process may be performed on a single piece, as opposed to, for example, performing a separate micro-tomography process on each specimen (which would tend to be more costly). This also advantageously tends to provide that a single three-dimensional model comprising all three test specimens is created. Thus, model analysis and the determination as to whether or not the quality criteria are satisfied tend to be facilitated. The different cross sections of the test specimens tend to facilitate differentiation of the specimens in the model.

The above described methods and apparatus advantageously tend to provide a measurement or metric that is indicative of the quality, or integrity, of the repair. For example, parameters corresponding to the one or more quality criteria (e.g. total defect volume, Number of defects, size, volume, shape & distribution of defects across the test specimen, total defect surface area, etc.) may be used as an indication of the integrity of the repair. Also, these parameters may be used to infer useful information about defects in the repaired object. The information gathered from multiple samples/repairs may also provide a record that may aid in the understanding of which characteristics are indicative of a good or poor repair. This tends to facilitate process refinement. These advantages tend to be particularly beneficial for AM processes, and in particular ones related to repairing damaged portions, because for example the objects may be relatively complex but simpler test specimens can conveniently be provided.

After undergoing the above described micro-tomography process, in some embodiments, one or more of the test specimens are used as mechanical test specimens, for example as an impact, or shear test specimen. The results of impact or shear tests performed on a test specimen may be used to assess, e.g., the mechanical strength of the repair, and provide a further indication of the integrity or quality of the repair build.

The accuracy with which the test specimens have been produced, and/or surface characteristics of the test specimens may also be measured. This may be used as a measure of the geometrical accuracy of the AM apparatus, and may indicate the quality of AM apparatus optics.

In the above embodiments, the first specimen is produced prior to the deposition of repair material within the void. Thus, the first specimen may be used to determine whether or not, before commencement of the repair process (and/or during initial stages of the repair process), the AM apparatus was operating as desired. Also the second specimen is produced during the repair of the object. Thus, the second specimen may be used to assess whether or not, during the repair process, the AM apparatus was operating as desired.

Also the third specimen is produced after the repair of the object. Thus, the third specimen may be used to assess whether or not, after repair of the object (and/or during the latter stages of the repair process), the AM apparatus was operating as desired.

Apparatus, including the processor, for implementing the above arrangement, and performing the method steps of FIG. 1, may be provided by configuring or adapting any suitable apparatus, for example one or more computers or other processing apparatus or processors, and/or providing additional modules. The apparatus may comprise a computer, a network of computers, or one or more processors, for implementing instructions and using data, including instructions and data in the form of a computer program or plurality of computer programs stored in or on a machine readable storage medium such as computer memory, a computer disk, ROM, PROM etc., or any combination of these or other storage media.

It should be noted that certain of the process steps depicted in the flowchart of FIG. 1 and described above may be omitted or such process steps may be performed in differing order to that presented above and shown in FIG. 1. Furthermore, although all the process steps have, for convenience and ease of understanding, been depicted as discrete temporally-sequential steps, nevertheless some of the process steps may in fact be performed simultaneously or at least overlapping to some extent temporally.

In the above embodiments, the object is made of metal. Also, the AM process is performed to add metal material to the object. However, in other embodiments the object is made of a different material, e.g. plastic, ceramics Also, an AM process may be performed to add a different material to the object. Also, an AM process may be performed to apply a customised repair material or alloy that has desirable or improved mechanical properties over and above that of the base material In the above embodiments, the AM process performed is a laser blown powder AM process in which powder is blown onto a weld pool on an object that has been created by a laser. However, in other embodiments, the AM process is a different type of AM process, for example, a powder bed fusion process, a sheet lamination process, a vat photopolymerisation process, a Laser Powder Bed process, or an AM process that implements Wire and Arc technologies.

In the above embodiments, the virtual model of the specimens is created using a micro-tomography (or micro-CT scanning) process. However, in other embodiments, the virtual model of the specimens is created using a different type of process.

In the above embodiments, the specimens are the size and shape described above. However, in other embodiments one or more of the specimens is a different size and/or shape to that described above.

In the above embodiments, three specimens are created. In particular, test specimens are created before, during, and after the performance of the AM repair process. However, in other embodiments a different number of specimens are created. For example, more than three test specimens may be created. Also, in other embodiments, the specimens may be created at different stages during the AM process. For example, in other embodiments, all of the specimens may be built during the performance of the AM process.

In the above embodiments, the specimens are created as a single column or stack. Also, in this embodiment, the specimens are CT scanned (i.e. X-rayed) as a single piece. However, in other embodiments, one or more of the specimens may be built as a separate item from the other specimens, or may be separated from one or more of the other specimens after being built. Also, in other embodiments, one or more of the specimens may be CT-scanned separately from one or more of the other specimens, so that a separate digital model of that one or more specimens is created.

In the above embodiments, the AM process is performed to repair a damaged object. However, in other embodiments, the AM process is performed to create a new object, or add additional features to an existing object.

What is claimed is:

1. A method of producing and assessing at least part of an object (2), the method comprising:
   providing an initial object; and
   performing, using common Additive Manufacturing apparatus (8), an Additive Manufacturing process to:
   add additional material to the initial object; and
   produce a test specimen (30, 34, 38), the test specimen (30, 34, 38) being produced from the same material as the additional material that is added to the initial object, the test specimen (30, 34, 38) being produced on a surface of the initial object at a location that is at or proximate to the location, on the initial object, of the additional material that is added by the Additive Manufacturing apparatus (8) performing the Additive Manufacturing process;
   performing, using computed-tomography apparatus (40), on the produced test specimen (30, 34, 38), a computed-tomography process to create a model (50), the model (50) being a digital model of the internal structure of the test specimen (30, 34, 38);
   determining whether or not the model (50) satisfies one or more criteria; and
   if the model (50) satisfies the one or more criteria, determining that the additional material added to the initial object is acceptable; or
   if the model (50) does not satisfy the one or more criteria, determining that the additional material added to the initial object is not acceptable.

2. The method according to claim 1, wherein a portion of the test specimen (30) is produced, by the Additive Manufacturing apparatus (8) performing the Additive Manufacturing process, before the Additive Manufacturing apparatus (8) has begun to add the additional material to the initial object.

3. The method according to claim 1, wherein a portion of the test specimen (30) is produced, by the Additive Manufacturing apparatus (8) performing the Additive Manufacturing process, after the Additive Manufacturing apparatus (8) has begun to add the additional material to the initial object and before the Additive Manufacturing apparatus has finished adding the additional material to the initial object.

4. The method according to claim 1, wherein a portion of the test specimen (38) is produced, by the Additive Manufacturing apparatus (8) performing the Additive Manufacturing process, after the Additive Manufacturing apparatus (8) has finished adding the additional material to the initial object.

5. The method according to claim 1, wherein
   the test specimen (30, 34, 38) comprises two or more portions selected from the group consisting of:
   a portion (30) that is produced, by the Additive Manufacturing apparatus (8) performing the Additive Manufacturing process, before the Additive Manufacturing apparatus (8) has begun to add the additional material to the initial object;

a portion (34) that is produced, by the Additive Manufacturing apparatus (8) performing the Additive Manufacturing process, after the Additive Manufacturing apparatus (8) has begun to add the additional material to the initial object and before the Additive Manufacturing apparatus has finished adding the additional material to the initial object; and a portion (38) that is produced, by the Additive Manufacturing apparatus (8) performing the Additive Manufacturing process, after the Additive Manufacturing apparatus (8) has finished adding the additional material to the initial object; and the portions of the test specimen (30, 34, 38) are created as a stack of contiguous portions.

6. The method according to claim 5, wherein each portion has a differently shaped cross-sectional area to the one or more other portions with which that portion is contiguous.

7. The method according to claim 1, wherein the step of determining whether or not the model (50) satisfies one or more criteria comprises:

analysing the model (50) to detect features (52) in the model (50) that correspond to defects with the test specimen (30, 34, 38); and determining whether or not the detected model features (52) satisfy the one or more criteria.

8. The method according to claim 7, wherein the features (52) are voids within the test specimen (30, 34, 38).

9. The method according to claim 7, wherein each of the one or more criteria is a criterion selected from the group of criteria consisting of:

a criterion that the total volume of the detected model features (52) is below a first pre-determined threshold value;

a criterion that the total surface area of the detected model features (52) is below a second pre-determined threshold value;

a criterion that the maximum volume of a detected model features (52) is below a third pre-determined threshold value;

a criterion that the maximum length of a detected model features (52) is below a fourth pre-determined threshold value;

a criterion that the total number of detected model features (52) is below a fifth pre-determined threshold value; and a criterion that the detected model features (52) are not arranged in a predetermined pattern.

10. The method according to claim 1, the method further comprising:

after the production of the test specimen (30, 34, 38), performing, using the Additive Manufacturing apparatus (8), an Additive Manufacturing process to produce a further test specimen, the further test specimen being produced from the same material as the additional material that is added to the initial object;

performing, using the computed-tomography apparatus, a computed-tomography process to create a further model, the further model being a digital model of the internal structure of the further test specimen;

determining whether or not the further model satisfies the one or more criteria; wherein the at least part of the object (2) produced by performing the Additive Manufacturing process is only acceptable if the both the model (50) and the further model satisfy the one or more criteria; and at least some of the at least part (2) of the object is produced, by the Additive Manufacturing apparatus performing the Additive Manufacturing process, between the production of the test specimen (30, 34, 38) and the production of the further test specimen.

11. The method according to claim 1, wherein the Additive Manufacturing process is a process selected from the group of Additive Manufacturing processes consisting of: a blown powder Additive Manufacturing process, a powder bed fusion Additive Manufacturing process, a sheet lamination Additive Manufacturing process, a vat photopolymerisation Additive Manufacturing process, a laser blown powder Additive Manufacturing process, a laser powder bed Additive Manufacturing process, and an Additive Manufacturing process that implemented wire and arc technology.

* * * * *